United States Patent
Peng et al.

(10) Patent No.: US 11,739,113 B2
(45) Date of Patent: Aug. 29, 2023

(54) **METHOD FOR EXTRACTING AND SEPARATING FLAVONOIDS FROM *LINDERA AGGREGATA* LEAVES**

(71) Applicant: Ningbo Municipal Hospital of T.C.M., Zhejiang (CN)

(72) Inventors: Xin Peng, Ningbo (CN); Chu Chu, Ningbo (CN); Yanfang Zou, Ningbo (CN); Shengqiang Tong, Ningbo (CN)

(73) Assignee: Ningbo Municipal Hospital of T.C.M., Ningbo (CN)

( * ) Notice: Subject to any disclaimer, the term of this patent is extended or adjusted under 35 U.S.C. 154(b) by 0 days.

(21) Appl. No.: 17/752,168

(22) Filed: May 24, 2022

(65) Prior Publication Data
US 2023/0147050 A1 May 11, 2023

(30) Foreign Application Priority Data
Nov. 10, 2021 (CN) .......................... 202111330523.9

(51) Int. Cl.
*C07H 1/08* (2006.01)
*B01D 15/18* (2006.01)
*C07H 17/07* (2006.01)

(52) U.S. Cl.
CPC ............ *C07H 1/08* (2013.01); *B01D 15/1807* (2013.01); *C07H 17/07* (2013.01); *B01D 2215/028* (2013.01)

(58) Field of Classification Search
CPC ...... C07H 1/08; C07H 17/07; B01D 15/1807; B01D 2215/028
See application file for complete search history.

(56) References Cited

PUBLICATIONS

Liu et al., Chinese Journal of Chromatography, 2007, 5, p. 735-739, English abstract only. (Year: 2007).*
Yang, J.Y., A Flavonoid Study of the Lauraceae, Thesis, U. British Columbia, 1998, 118 pages (Year: 1998).*
Li et al., Talanta, 2013, 105, p. 393-402. (Year: 2013).*

\* cited by examiner

*Primary Examiner* — Jonathan S Lau
(74) *Attorney, Agent, or Firm* — Harness, Dickey & Pierce, P.L.C.

(57) ABSTRACT

The present disclosure provides a method for extracting and separating flavonoids from *Lindera aggregata* leaves. The method includes: mixing *Lindera aggregata* leaves with an adsorbent, conducting elution with a matrix solid-phase dispersion (MSPD) extraction method, followed by concentration to obtain a *Lindera aggregata* leaf extract; conducting primary separation and secondary separation on the *Lindera aggregata* leaf extract by high-speed counter-current liquid chromatography (HSCCC), to separate quercetin-3-O-β-D-arabinofuranoside, a mixture of quercetin-3-O-β-D-glucoside and quercetin-5-O-β-D-glucoside, quercetin-3-O-rhamnopyranoside, and kaempferol-7-O-α-L-rhamnopyranoside; where a second solvent system used in the secondary separation includes ethyl acetate, n-butanol, an addictive and water, and the addictive includes cyclodextrin. The method has a short separation period, high separation efficiency, and less impurities during purification and separation of the flavonoids from the *Lindera aggregata* leaves.

9 Claims, 7 Drawing Sheets

METHOD FOR EXTRACTING AND SEPARATING FLAVONOIDS FROM *LINDERA AGGREGATA* LEAVES

CROSS REFERENCE TO RELATED APPLICATION

This patent application claims the benefit and priority of Chinese Patent Application No. 202111330523.9, filed on Nov. 10, 2021, the disclosure of which is incorporated by reference herein in its entirety as part of the present application.

TECHNICAL FIELD

The present disclosure belongs to the technical field of separation and purification, and relates to a method for extracting and separating flavonoids from *Lindera aggregata* leaves. In particular, the present disclosure relates to a high-efficiency and high-recovery method for extracting and separating flavonoids from *Lindera aggregata* leaves based on "amplified" matrix solid-phase dispersion (MSPD) extraction and high-speed counter-current liquid chromatography (HSCCC).

BACKGROUND ART

*Lindera aggregata* (Sims) Kosterm as a plant of genus *Lindera*, and family Lauraceae, is distributed in Jiangsu, Zhejiang, Taiwan, Fujian, Guangdong and other provinces. The most famous *Lindera aggregata* are distributed in Tiantai County, Zhejiang Province which are called Tiantai *Lindera aggregata*, with a yield accounting for 30% of the national *Lindera aggregata* products. Chinese Pharmacopoeia has recorded that the dried roots of *Lindera aggregata* can be used as a medicine. Meanwhile, stems and leaves of the *Lindera aggregata* are used in folk in China. Among them, the *Lindera aggregata* leaves were approved as a new food resource in 2012, and included in the new food raw material catalog by the National Health and Family Planning Commission of the PRC. Meanwhile, in-depth research and development of the *Lindera aggregata* leaves have attracted increasing attention. The *Lindera aggregata* leaves mainly contain flavonoids, and are reported to have pharmacological effects such as antioxidant, lipid-lowering, and antibacterial properties. Therefore, separation and acquisition of these flavonoids are very important for further researching the pharmacodynamic material basis of *Lindera aggregata* leaves.

A traditional extraction, separation and purification method of ingredients in the *Lindera aggregata* leaves mainly include: extracting target ingredients by a heating reflux method or an ultrasonic extraction method, followed by conducting separation and purification using column chromatography, preparative liquid chromatography and other methods. Although being classic, this separation strategy has disadvantage of long separation cycle, high solvent consumption, and cumbersome operation steps. Moreover, due to repeated use of the column chromatography, the separation has seriously irreversible adsorption, and a recovery rate of generally less than 50%, sometimes even less than 10%, leading to difficulty in obtaining some ingredients with a low content. For example, in the *Lindera aggregata* leaves, reference substances such as quercetin-5-O-β-D-glucoside and quercetin-3-O-β-D-glucoside are not commercially available, which hinder the further research and full utilization of *Lindera aggregata* leaves. Therefore, it is extremely important to develop a rapid, efficient and low-cost preparation method for the separation and purification of trace ingredients in the *Lindera aggregata* leaves.

High-speed counter-current liquid chromatography (HSCCC) is a highly-efficient and continuous liquid-liquid distribution technique commonly used in the separation and purification of natural products in recent years. Since no solid support is used as a stationary phase during the separation, the HSCCC has no irreversible adsorption or sample loss, and possess the advantages of high efficiency and rapidity. Yun Liu et al. reported a method for separating flavonoids from *Lindera aggregata* leaves by HSCCC. In the method, separation is conducted using n-hexane-n-butanol-ethyl acetate-glacial acetic acid-water (at a volume ratio of 2:2:5:1.5:6) as a two-phase solvent system, to obtain three monomers, quercetin-3-O-β-D-arabinofuranoside, quercetin-3-O-rhamnopyranoside, and kaempferol-7-O-α-L-rhamnopyranoside, and a mixture of a pair of isomers, quercetin-3-O-β-D-glucoside and quercetin-5-O-β-D-glucoside (Yun Liu, Guixin Chou. Isolation and Preparation of Flavonoids from the Leaves of *Lindera aggregata* Using High Speed Counter-Current Chromatography [J]. Chinese Journal of Chromatography, 2007 (05): 735-739). On this basis, the present disclosure explores a new biphasic solvent system, and proposes to separate the isomers quercetin-3-O-β-D-glucoside effectively from quercetin-5-O-β-D-glucoside using hydroxypropyl-β-cyclodextrin as additive. In addition, a traditional extraction method used for sample extraction before HSCCC separation is generally heating reflux extraction. Although HSCCC having a high separation and purification efficiency, the time-consuming and labor-intensive extraction method to obtain the crude extract before HSCCC, resulting in a reduced efficiency during the whole extraction, separation and purification process.

Matrix solid-phase dispersion (MSPD) extraction, as a novel sample pretreatment method, integrates extraction and purification into one step, possess the advantages of less solvent consumption, less environmental pollution, short extraction time, simple operation and high extraction efficiency. It has been widely used in quantitative analysis of food, environmental samples, and traditional Chinese medicines. There is no report on the application of MSPD extraction in extraction for the purpose of purification.

Therefore, it is urgent to develop an effective extraction and separation method of quercetin-3-O-β-D-arabinofuranoside, quercetin-3-O-β-D-glucoside, quercetin-5-O-β-D-glucoside, quercetin-3-O-rhamnopyranoside, and kaempferol-7-O-α-L-rhamnopyranoside in the *Lindera aggregata* leaves for its further research and full utilization.

SUMMARY

A main purpose of the present disclosure is to provide a fast and efficient method for extracting and separating flavonoids from *Lindera aggregata* leaves, thereby overcoming deficiencies of the current method.

To achieve the above purpose, the present disclosure adopts the following technical solutions.

The present disclosure provides a method for extracting and separating flavonoids from *Lindera aggregata* leaves, including the following steps:

mixing *Lindera aggregata* leaves with adsorbent uniformly, transferring the mixture to a column, and then eluting the target compounds by suitable solvent, after that, *Lindera aggregata* leaf crude extract is obtained after condensing the eluent;

conducting first separation on the *Lindera aggregata* leaf extract by HSCCC, to obtain quercetin-3-O-β-D-arabinofuranoside, a mixture of quercetin-3-O-β-D-glucoside and quercetin-5-O-β-D-glucoside, quercetin-3-O-rhamnopyranoside, and kaempferol-7-O-α-L-rhamnopyranoside; where a first solvent system consisting of ethyl acetate, n-butanol, n-hexane, glacial acetic acid, and water;

conducting secondary separation on the mixture of quercetin-3-O-β-D-glucoside and quercetin-5-O-β-D-glucoside by the HSCCC, to separate the quercetin-3-O-β-D-glucoside from the quercetin-5-O-β-D-glucoside; where a second solvent system including ethyl acetate, n-butanol, an additive and water, and the additive includes cyclodextrin.

Specifically, the second solvent system may include ethyl acetate, n-butanol, hydroxypropyl-β-cyclodextrin and water; and the hydroxypropyl-β-cyclodextrin and water may form an acidic aqueous solution with the concentration of hydroxypropyl-β-cyclodextrin is 0.05 mol/L.

The present disclosure further provides application of the method in rapid extraction, separation and purification of active ingredients in traditional Chinese medicine.

Compared with the prior art, the present disclosure has the following beneficial effects:

(1) In the present disclosure, the active ingredients from the traditional Chinese medicine "*Lindera aggregata* leaves" are extracted and separated using the MSPD extraction coupled with the HSCCC.

(2) In the present disclosure, under the optimal process conditions of MSPD extraction and the HSCCC, quercetin-3-O-β-D-arabinofuranoside, quercetin-3-O-β-D-glucoside, quercetin-5-O-β-D-glucoside, quercetin-3-O-rhamnopyranoside, and kaempferol-7-O-α-L-rhamnopyranoside can be separated and purified with high purities.

(3) In the present disclosure, the MSPD extraction and the HSCCC are combined to conduct extraction, separation and purification of complex matrices in the *Lindera aggregata* leaves for the first time.

BRIEF DESCRIPTION OF THE DRAWINGS

To describe the technical solutions in the examples of the disclosure or in the prior art more clearly, the accompanying drawings required for describing the examples or the prior art will be described briefly below. Apparently, the accompanying drawings in the following description show some examples of the disclosure, and a person of ordinary skill in the art may still derive other drawings from these accompanying drawings without creative efforts.

DETAILED DESCRIPTION OF THE EMBODIMENTS

Figure 1:
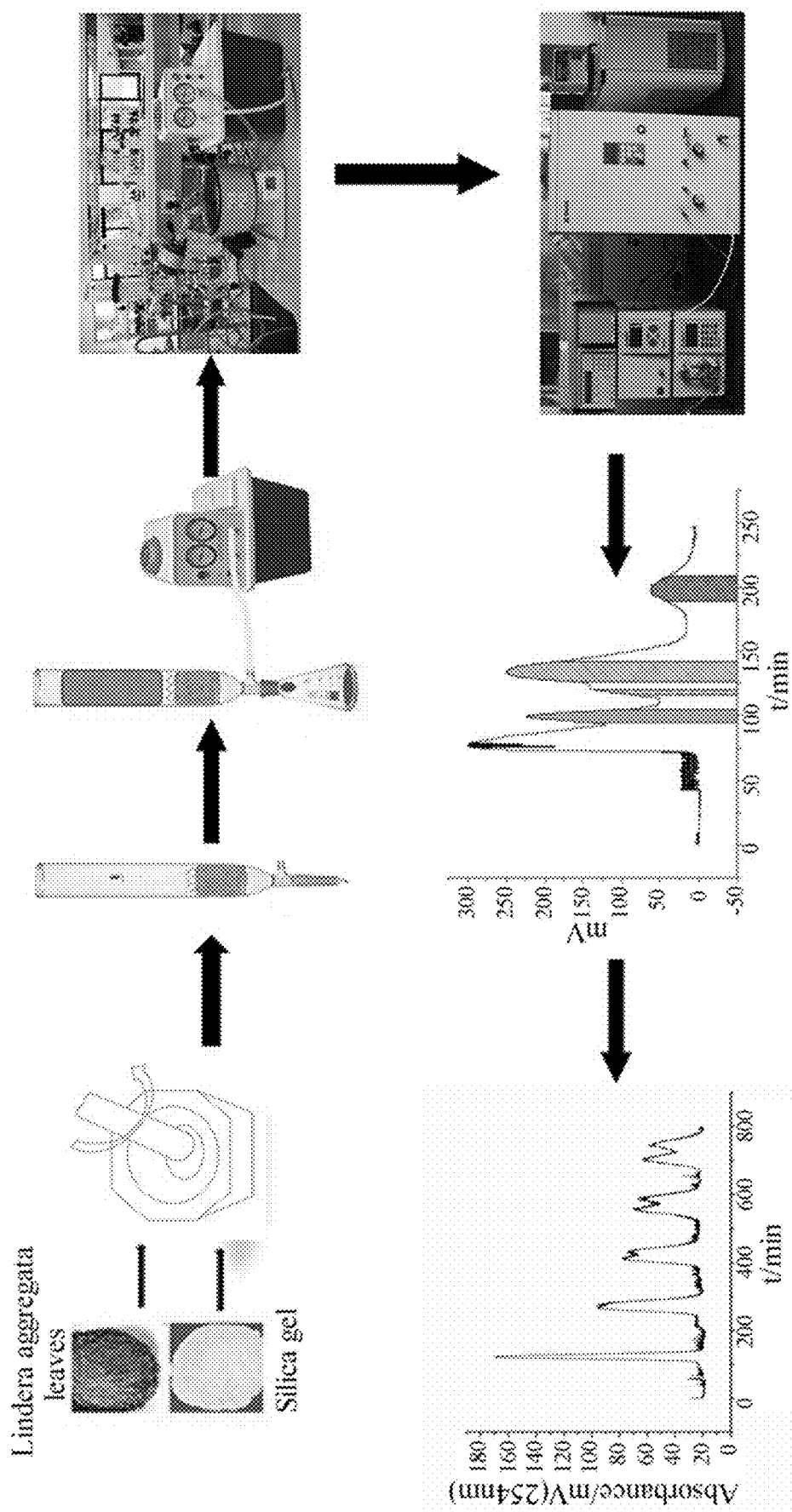
FIG. 1 shows a process flow diagram of a strategy combining "amplified" MSPD extraction with HSCCC in an exemplary example of the present disclosure.

In view of defects in the prior art, the inventor of this application has been able to propose the technical solutions of the present disclosure after long-term research and extensive practice. The technical solutions of the present disclosure will be described clearly and completely below. Obviously, the described examples are part rather than all of the examples in the present disclosure. All other examples obtained by a person of ordinary skill in the art based on the examples of the present disclosure without creative efforts shall fall within the protection scope of the present disclosure.

Specifically, as an aspect of the technical solutions, the present disclosure provides a method for extracting and separating flavonoids from *Lindera aggregata* leaves, including the following steps:

extracting *Lindera aggregata* leaves by a MSPD extraction method, that is: mixing the *Lindera aggregata* leaves with an adsorbent uniformly, conducting elution using a suitable solvent, and conducting concentration to obtain a *Lindera aggregata* leaf extract;

conducting primary separation on the *Lindera aggregata* leaf extract by HSCCC, to obtain quercetin-3-O-β-D-arabinofuranoside, a mixture of quercetin-3-O-β-D-glucoside and quercetin-5-O-β-D-glucoside, quercetin-3-O-rhamnopyranoside, and kaempferol-7-O-α-L-rhamnopyranoside; where a first solvent system used in the primary separation includes ethyl acetate, n-butanol, n-hexane, glacial acetic acid, and water; and conducting secondary separation on the mixture of quercetin-3-O-β-D-glucoside and quercetin-5-O-β-D-glucoside by the HSCCC, to separate the quercetin-3-O-β-D-glucoside from the quercetin-5-O-β-D-glucoside; where a second solvent system used in the secondary separation includes the ethyl acetate, the n-butanol, an additive and water, and the additive includes cyclodextrin.

Further, the cyclodextrin includes hydroxypropyl-β-cyclodextrin, and is not limited thereto.

Preferably, the method specifically includes: conducting the primary separation on the *Lindera aggregata* leaf extract by the HSCCC, collecting eluates at 105 min to 115 min, 120 min to 130 min, 170 min to 185 min, and 270 min to 290 min, separately, to obtain quercetin-3-O-β-D-arabinofuranoside, the mixture of quercetin-3-O-β-D-glucoside and quercetin-5-O-β-D-glucoside, quercetin-3-O-rhamnopyranoside, the kaempferol-7-O-α-L-rhamnopyranoside; where the HSCCC is conducted at 800 rpm, 25° C., and an ultraviolet detection wavelength of 280 nm and by using an upper phase as a stationary phase with a retention value of 20% to 40%, and a lower phase as a mobile phase with a flow rate of 2 mL/min.

Preferably, in the first solvent system, ethyl acetate, n-butanol, n-hexane, the glacial acetic acid and water have a volume ratio of 5:2:2:1.5:6.

Preferably, the method specifically includes: conducting the secondary separation on the mixture of quercetin-3-O-β-D-glucoside and quercetin-5-O-β-D-glucoside by the HSCCC, collecting eluates at 670 min to 710 min and 740 min to 790 min, separately, to separate quercetin-3-O-β-D-glucoside from quercetin-5-O-β-D-glucoside; where the HSCCC is conducted at 800 rpm, 5° C., and an ultraviolet detection wavelength of 254 nm and by using an upper phase as a stationary phase with a retention value of 25% to 50%, and a lower phase as a mobile phase with a flow rate of 2 mL/min.

Preferably, the second solvent system includes ethyl acetate, n-butanol, hydroxypropyl-p-cyclodextrin and water; and the hydroxypropyl-p-cyclodextrin and water form an acidic aqueous solution of the hydroxypropyl-p-cyclodextrin with a concentration of 0.05 mol/L.

Further, the aqueous solution of the hydroxypropyl-p-cyclodextrin has a pH value of 3.16; and the ethyl acetate, the n-butanol, and the aqueous solution of the hydroxypropyl-p-cyclodextrin have a volume ratio of 9:1:10.

Preferably, the *Lindera aggregata* leaves and the adsorbent have a mass ratio of 1:0 to 2:1.

Further, the *Lindera aggregata* leaves and the adsorbent have the mass ratio of 1:1.

Preferably, the adsorbent includes any one or a combination of two or more selected from the group consisting of silica gel, alumina, Florisil, and molecular sieve SBA-15, and is not limited thereto.

Further, the adsorbent is the silica gel.

Preferably, the method specifically includes the following steps:

drying, pulverizing, sieving the *Lindera aggregata* leaves, and mixing with the adsorbent for grinding, to form a *Lindera aggregata* leaf mixture;

conducting elution on the *Lindera aggregata* leaf mixture in a chromatographic column to obtain a *Lindera aggregata* leaf eluate; and concentrating and drying the *Lindera aggregata* leaf eluate to obtain the *Lindera aggregata* leaf extract.

Further, the sieving is conducted at 65 mesh.

Further, the grinding is conducted for 0 min to 6 min.

Preferably, an eluent used in the elution includes any one of ethanol, 70% ethanol, methanol, 50% methanol, 70% methanol, and 90% methanol.

Further, the eluent used in the elution is the 70% ethanol.

Further, the eluent has a flow rate of 0.5 mL/min to 3 mL/min.

Furthermore, the eluent has the flow rate of 1 mL/min.

Further, the eluent has a volume of 1 BV to 6 BV.

Furthermore, the eluent has the volume of 5 BV.

More preferably, the method for extracting and separating flavonoids from *Lindera aggregata* leaves includes the following steps:

(1) subjecting *Lindera aggregata* leaves to drying, pulverizing, and sieving at 65 mesh to obtain a *Lindera aggregata* leaf powder;

(2) weighing the *Lindera aggregata* leaf powder and an adsorbent at a certain mass ratio in a mortar, and grinding for a certain time; transferring a ground solid mixture to a suction filtration chromatographic column, and spreading an appropriate amount of absorbent cotton on a top of the solid mixture; adding an eluent, pressurizing for elution, and collecting an eluate for concentration; where the adsorbent is the silica gel;

(3) separating a concentrated and dried extract by HSCCC, and collecting eluates in sections;

(4) subjecting the collected eluates to HPLC for detection; and (5) concentrating and crystallizing the eluates to obtain products of quercetin-3-O-β-D-arabinofuranoside, quercetin-3-O-β-D-glucoside, quercetin-5-O-β-D-glucoside, quercetin-3-O-rhamnopyranoside, and kaempferol-7-O-α-L-rhamnopyranoside.

Further, in step (2), the *Lindera aggregata* leaf powder and the silica gel has a mass ratio of 1:0 to 2:1, preferably 1:1.

Further, in step (2), the grinding is conducted with a mortar for 0 min to 6 min, preferably 4 min.

Further, in step (2), the eluent is selected from one of ethanol, 70% ethanol, methanol, 50% methanol, 70% methanol, and 90% methanol, preferably the 70% ethanol.

Further, in step (2), the eluent has a flow rate of 0.5 mL/min to 3 mL/min, preferably 1 mL/min.

Further, in step (2), the eluent has a volume of 1 BV to 6 BV, preferably 5 BV.

Further, in step (3), in the method for separating and extracting quercetin-3-O-β-D-arabinofuranoside, quercetin-3-O-β-D-glucoside and quercetin-5-O-β-D-glucoside, the quercetin-3-O-rhamnopyranoside, and the kaempferol-7-O-α-L-rhamnopyranoside from the *Lindera aggregata* leaves by the HSCCC, the first solvent system used in the HSCCC includes ethyl acetate, n-butanol, n-hexane, glacial acetic acid and water at a volume ratio of 5:2:2:1.5:6, and the HSCCC is conducted at 800 rpm, 25° C., and an ultraviolet detection wavelength of 280 nm and by using an upper phase as a stationary phase with a retention value of 20% to 40%, and a lower phase as a mobile phase with a flow rate of 2 mL/min; after injection, the eluates are collected at 105 min to 115 min, 120 min to 130 min, 170 min to 185 min, and 270 min to 290 min, separately. A mixture of quercetin-3-O-β-D-glucoside and the quercetin-5-O-β-D-glucoside was obtained from the above solvent system.

Further, quercetin-3-O-β-D-glucoside and quercetin-5-O-β-D-glucoside are separated using a second solvent system including ethyl acetate, n-butanol and a 0.05 mol/L cyclodextrin aqueous solution at a volume ratio of 9:1:10, where the HSCCC is conducted at 800 rpm, 5° C., and an ultraviolet detection wavelength of 254 nm and by using an upper phase as a stationary phase with a retention value of 25% to 50%, and a lower phase as a mobile phase with a flow rate of 2 mL/min; after injection, the eluates are collected at 670 min to 710 min and 740 min to 790 min, separately.

In the present disclosure, FIG. 1 shows a process flow diagram of a strategy by combining the amplified MSPD extraction with the HSCCC for extraction and separation of *Lindera aggregata* leaves.

As another aspect of the technical solutions, the present disclosure further provides the application of the method in rapid extraction, separation and purification of active ingredients in traditional Chinese medicine.

In the present disclosure, the MSPD extraction that integrates extraction and purification into one step was combined with the HSCCC for the first time, and the hydroxypropyl-β-cyclodextrin is used as an additive in a two-phase solvent system, thereby efficiently extracting and separating quercetin-3-O-β-D-arabinofuranoside, quercetin-3-O-β-D-glucoside, quercetin-5-O-β-D-glucoside, quercetin-3-O-rhamnopyranoside, and kaempferol-7-O-α-L-rhamnopyranoside from the *Lindera aggregata* leaves. The amplified MSPD extraction, as a novel method for sample extraction, can greatly save extraction time and extraction solvents, and is friendly to thermally unstable ingredients. The HSCCC purification method can eliminate the solid phase support as a stationary phase, and has no irreversible adsorption, thereby greatly improving recovery of the separation on target ingredients. The method not only provides a more environmental-friendly, cheaper, faster, simpler and more efficient new method for the extraction and separation of active ingredients from the *Lindera aggregata* leaves, but also provides an effective strategy for the rapid extraction, separation and purification of active ingredients in other traditional Chinese medicines.

In the present disclosure, a strategy combining the MSPD extraction and the HSCCC separation and purification is proposed for the first time, to separate and purify the ingredients in traditional Chinese medicines/natural medicines, with a high efficiency and high recovery rate; the MSPD extraction is only used as an extraction method for sample analysis in existing reports, and there is no report on the MSPD extraction as an extraction, separation and purification method; and the HSCCC separation and purification of two flavonoid isomers has not been reported in the literature. In this method, two difficult-to-separate ingredients are successfully separated by adding the additive cyclodextrin to the biphasic solvent system.

In the following, examples of the present disclosure will be described in detail. The examples are implemented on the premise of the technical solutions of the present disclosure, and detailed implementations and specific operation processes are provided, but the protection scope of the present disclosure is not limited to the following examples.

The experimental materials used in the following examples can be purchased from conventional biochemical reagent companies unless otherwise specified.

In the examples, the silica gel $mSiO_2 \cdot nH_2O$ is preferably purchased from ANPEL Laboratory Technologies (Shanghai) Inc.

In the examples, the $C_{18}$ is purchased from Shanghai Zhengya Chemical Co., Ltd.

In the examples, the instrument used is an Agilent 1260 Infinity LC, Agilent Technologies, Santa Clara, Calif., USA, equipped with a vacuum pump, a binary mobile phase system, a constant-temperature autosampler, and a constant-temperature column oven. A chromatographic column is a Kromasil 100-5$C_{18}$ chromatographic column (250 mm×4.6 mm, 5 μm), with a column temperature of 30° C. The mobile phase is acetonitrile (B) and 0.1% aqueous solution of formic acid (D), gradient elution is as follows: 0 min, 10% B, 15 min, 15% B, 23 min, 23% B, 40 min, 29% B, 41 min, 70% B, 43 min, 100% B, and 46 min, 100% B; a running time is 46 min; an injection volume is: 10 μL, a flow rate is: 1 mL/min, and a detection wavelength is: 280 nm.

In the examples, an HSCCC instrument is a TBE-200V J-type HSCCC instrument (Tauto Biotechnique, Shanghai, China). A HSCCC system includes three multi-layer coils, an MP-0106 constant-current pump, a 21C-B UV detector and an SDC-6 constant-temperature controller, and a workstation includes a BSZ-160 automatic component collector and SEPU3010. An initial separation column includes a 1.6 mm ID PTFE tubing with a total volume of 190 mL. A β value for the column varies from 0.45 to 0.81.

Example 1 Selection of Adsorbent Types 4 parts of 30 mg of a *Lindera aggregata* leaf powder were added into 4 groups of agate mortars in parallel, separately, and 30 mg of different adsorbents (Florisil, Ningbo Hongpu Instrument Technology Co., Ltd.), a molecular sieve SBA-15 (Nanjing JCNANO Tech Co., Ltd.), $Al_2O_3$ (ANPEL Laboratory Technologies (Shanghai) Inc.), and Silica gel (ANPEL Laboratory Technologies (Shanghai) Inc.) were added to the 4 groups of mortars, separately, and ground with the *Lindera aggregata* leaf powder for 3 min. A ground solid mixture was passed through a matrix solid-phase cartridge (with a gasket), and 2 mL of 70% ethanol was added for pressure elution; an eluate was collected, concentrated, and dissolved in 1 mL of methanol, and centrifuged at 13,000 rpm for 5 min; a supernatant obtained by centrifugation was collected, and put into a sample vial, for detection and analysis by HPLC.

Figure 2A:
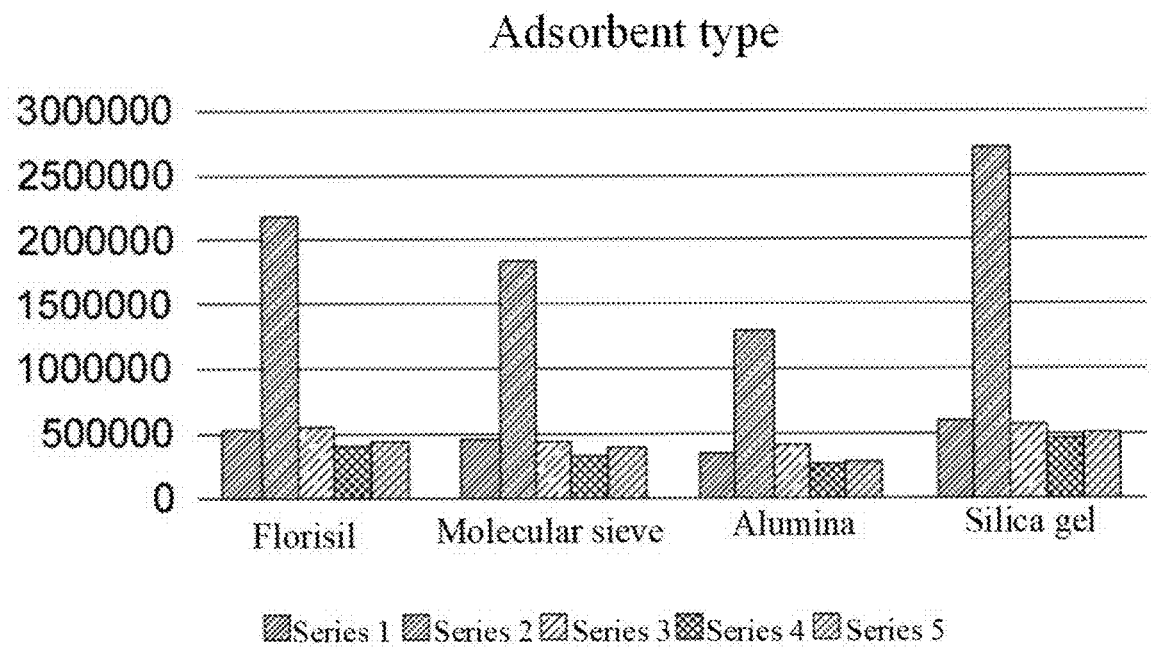
FIG. 2a to FIG. 2f show effect diagrams of different conditions in the MSPD extraction on influences of the extraction in Examples 1-5 of the present disclosure.

During the adsorption of MSPD, the adsorbent was an important factor affecting the extraction efficiency, which not only served as a solid support but also played a role in the adsorption and separation of target compounds. In this experiment, the effects of molecular sieve SBA-15 and conventional adsorbents, Florisil, $Al_2O_3$, and silica gel on the extraction efficiency of quercetin-3-O-β-D-arabinofuranoside, quercetin-3-O-β-D-glucoside, quercetin-5-O-β-D-glucoside, quercetin-3-O-rhamnopyranoside, and kaempferol-7-O-α-L-rhamnopyranoside in the *Lindera aggregata* leaves were investigated. The results are shown in FIG. 2a. The results show that the extraction efficiency of silica gel for the target analyte is higher than that of molecular sieve SBA-15, $Al_2O_3$ and Florisil, such that the silica gel is selected as the adsorbent.

Example 2 Selection of a Mass Ratio of Samples to Adsorbents 4 parts of 30 mg of *Lindera aggregata* leaf powder were added to 4 groups of agate mortars in parallel, separately, and silica gels of different mass (0 mg, 15 mg, 30 mg, and 60 mg) were added to the 4 groups of mortars, separately, and ground with the *Lindera aggregata* leaf powder for 3 min. A ground solid mixture was passed through a matrix solid-phase cartridge (with a gasket), and 2 mL of 70% ethanol was added for pressure elution; an eluate was collected, concentrated, and dissolved in 1 mL of methanol, and centrifuged at 13,000 rpm for 5 min; a supernatant obtained by centrifugation was collected, and put into a sample vial for detection and analysis by HPLC.

Figure 2B:
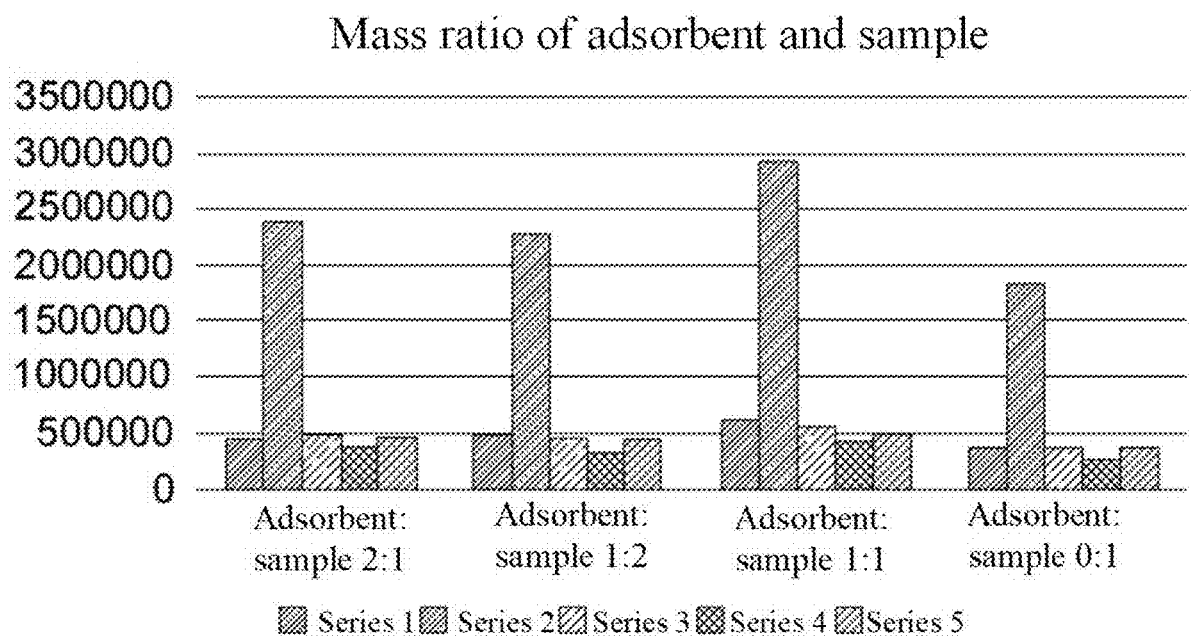

The extraction effects of different mass ratios of sample to adsorbent are shown in FIG. 2b. The results show that the extraction efficiency of the target analyte gradually increases when the mass ratio of sample to adsorbent increases from 1:0 to 1:1. When the mass ratio increases to 1:2, the extraction efficiency begins to decline, such that 1:1 is selected as the mass ratio of sample to adsorbent.

Example 3 Selection of Elution Solvents 6 parts of 30 mg of a *Lindera aggregata* leaf powder and 6 parts of 30 mg of silica gel were added to 2 groups of agate mortars, and ground for 3 min, separately. A ground solid mixture was passed through a matrix solid-phase cartridge (with a gasket), and 2 mL of ethanol, 70% ethanol, methanol, 50% methanol, 70% methanol, and 90% methanol, preferably the 70% ethanol was added as an eluent for pressure elution; an eluate was collected, concentrated, and dissolved in 1 mL of 70% methanol, and centrifuged at 13,000 rpm for 5 min; a supernatant obtained by centrifugation was collected, and put into a sample vial for detection and analysis using a high performance liquid chromatography.

Figure 2C:
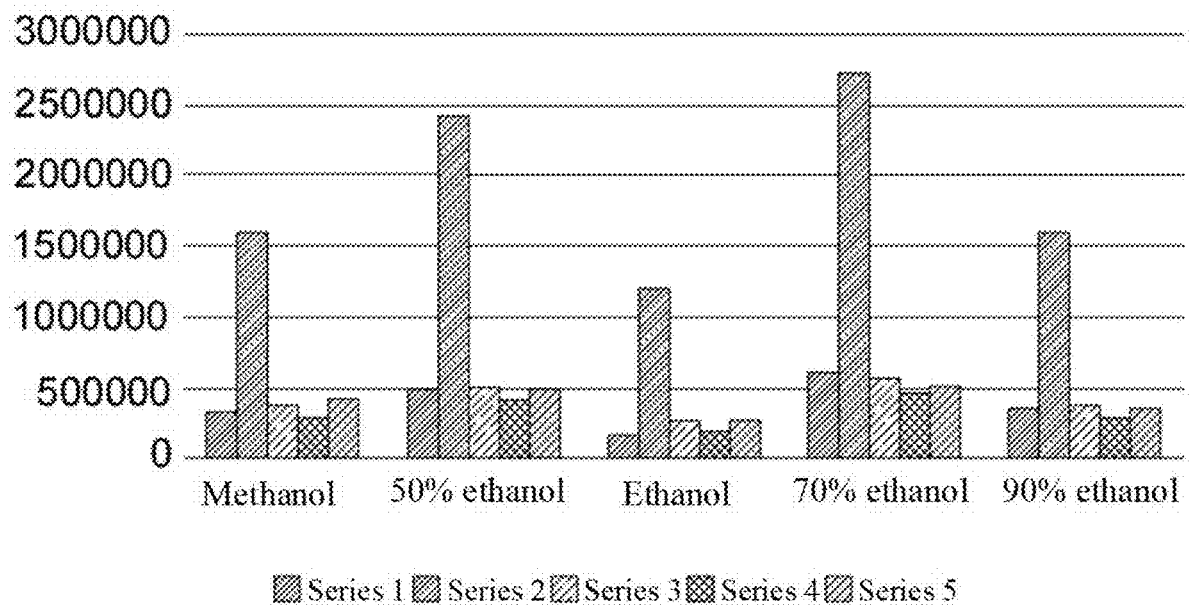

The extraction efficiency of different elution solvents are shown in FIG. 2c. The results show that the elution efficiency of 70% ethanol as the elution solvent for three analytes is higher than that of the methanol, 50% methanol, 70% methanol, 90% methanol and ethanol. The 70% ethanol is preferred, and selected as the eluent in further research.

Example 4 Adsorption Kinetic Test 4 parts of 5 g of a *Lindera aggregata* leaf powder and 4 parts of 5 g of silica gel were added to 4 groups of agate mortars, and ground for different times (0 min, 2 min, 4 min, and 6 min), separately. A ground solid mixture was transferred to a suction filtration chromatographic column, and an appropriate amount of absorbent cotton was placed below and above the solid mixture, 125 mL of a 70% ethanol eluent was added for pressure elution; an eluate was collected, concentrated, and dissolved in 150 mL of 70% methanol, and centrifuged at 13,000 rpm for 4 min; a supernatant obtained by centrifugation was collected, and put into a sample vial for detection and analysis using a high performance liquid chromatography.

Figure 2D:
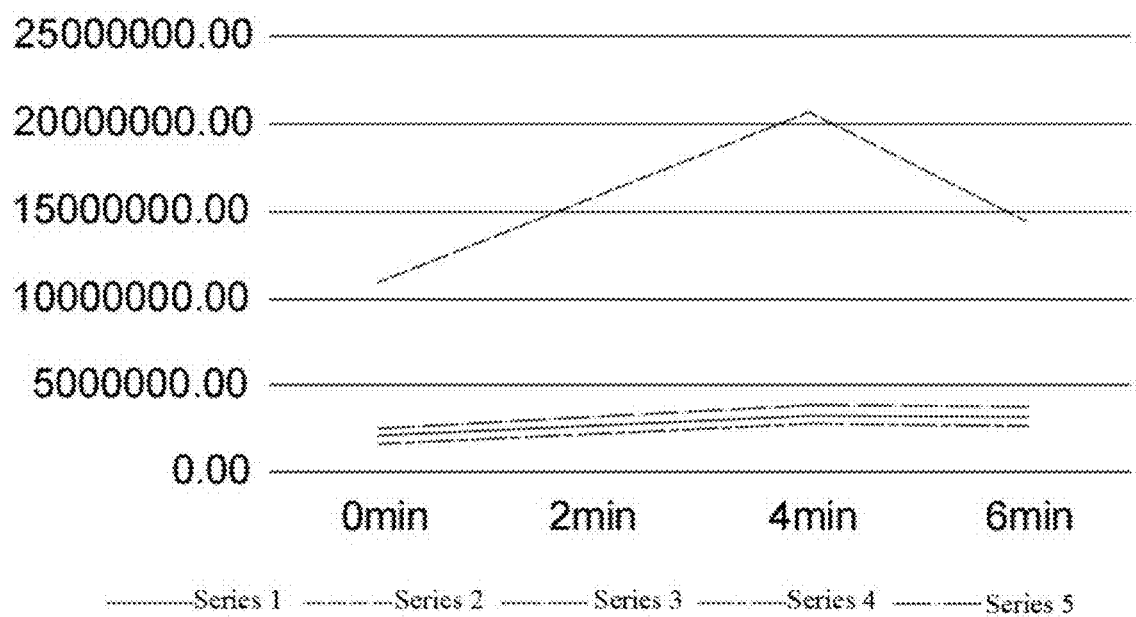

The extraction efficiency of different grinding times is shown in FIG. 2d. The results show that the extraction efficiency is enhanced with the increase of grinding time, and reaching an optimal value after 4 min; but when the grinding time is extended to 6 min, the extraction efficiency decreases instead. The reason may be that the active ingredients are over-extracted and squeezed into dense pores in the adsorbent due to an excessive grinding time, which increases the difficulty of elution and reduces the extraction efficiency.

Example 5 Kinetic Test (Selection of an Elution Rate and an Eluent Volume)

(1) Selection of an Elution Rate 6 parts of 5 g of a *Lindera aggregata* leaf powder and 6 parts of 5 g of silica gel were added to 6 groups of agate mortars, separately, and ground for 4 min. A ground solid mixture was transferred to a suction filtration chromatographic column, and an appropriate amount of absorbent cotton was placed above the solid mixture, 150 mL of a 70% ethanol eluent was added for pressure elution at flow rates (0.5 mL/min, 1 mL/min, 2 mL/min, and 3 mL/min), separately; an eluate was collected, concentrated, and dissolved in 150 mL of methanol, and centrifuged at 13,000 rpm for 5 min; a supernatant obtained by centrifugation was collected, and put into a sample vial, for detection and analysis using a high performance liquid chromatography.

Figure 2E:
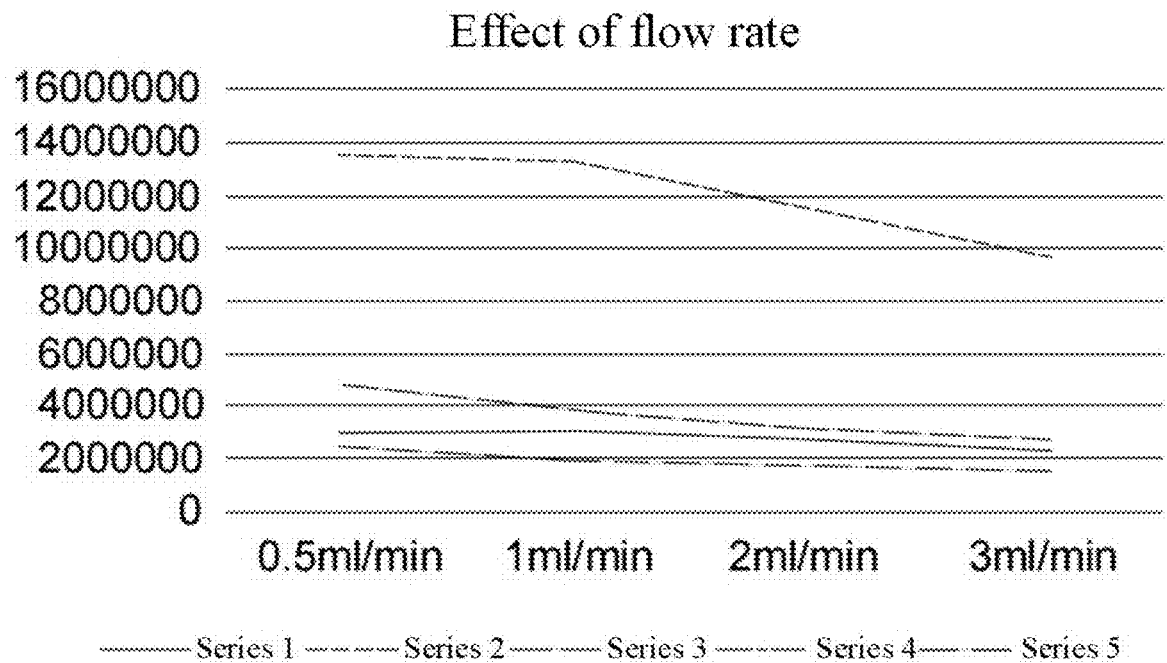

The extraction efficiency of the eluent at different rates is shown in FIG. 2e. When the eluent volume is gradually increased from 1 mL/min to 6 mL/min, the extraction efficiency of the target analyte is not as good as that of 1 mL/min, such that 1 mL/min is selected as the elution rate in further research.

(2) Selection of an Elution Volume 5 g of a *Lindera aggregata* leaf powder and 5 g of silica gel were added to the agate mortar, separately, and ground for 4 min. A uniform solid mixture was carefully transferred to a suction filtration chromatographic column, and an appropriate amount of absorbent cotton was placed below and above the solid mixture, 150 mL of a 70% ethanol eluent was added for elution at a flow rate of 1 mL/min; one tube of eluent with a volume of 25 mL per column was collected, and a total of 6 tubes were collected (1 BV, 2 BV, 3 BV, 4 BV, 5 BV, and 6 BV), the 6 tubes of eluates were concentrated and dissolved in 15 mL of methanol, and centrifuged at 13,000 rpm for 5 min; a supernatant obtained by centrifugation was collected, and put into a sample vial, for detection and analysis using a high performance liquid chromatography.

Figure 2F:
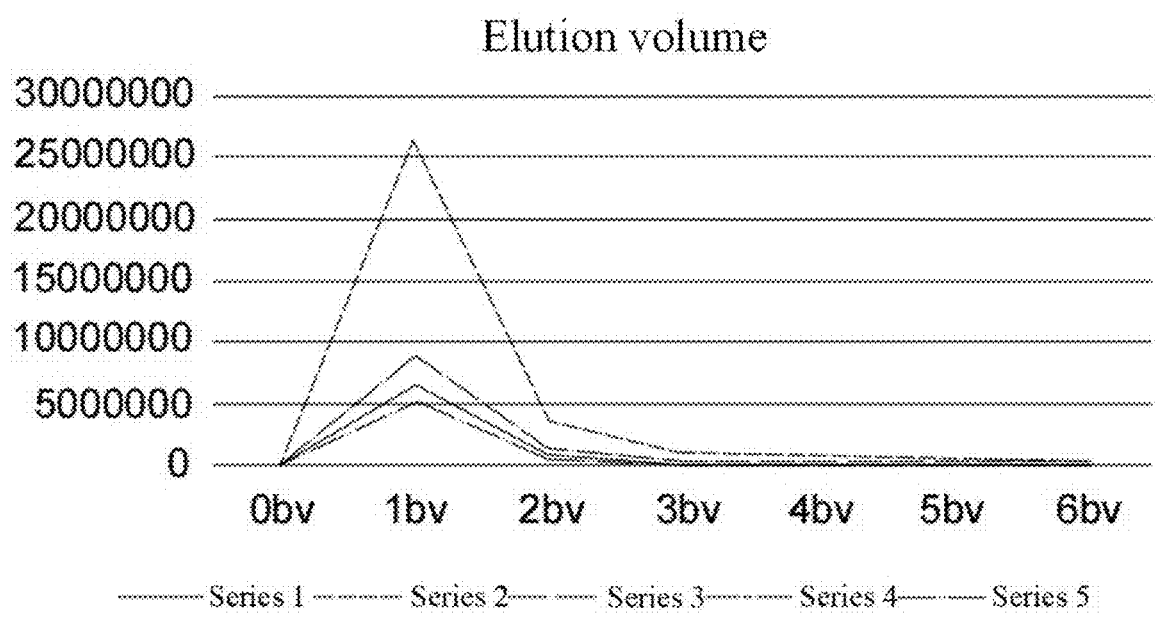

The extraction efficiencies of different eluent volumes are shown in FIG. 2f. When the volume of eluent is gradually increased from 1 BV to 6 BV, the extraction efficiency of the target analyte gradually increases; and when the volume is increased to 6 BV, the elution efficiency of the target component reaches a maximum. It shows that the eluent volume of 6 BV can elute the active ingredients on the silica gel to a greater extent, while keeping a relatively low solvent volume.

Example 6 Comparison of MSPD, "Amplified" MSPD and Refluxing on Extraction Efficiency The "amplified" MSPD with the sample amount of 5 g and MSPD with the sample amount of 30 mg were compared. The result showed after amplification, the extraction efficiency was almost the same. Moreover, as a conventional practice for extracting effective ingredients, refluxing was used to be compared with the developed "amplified" MSPD on extraction efficiency. The result clearly showed "amplified" MSPD achieved almost the same extraction efficiency with refluxing, but with much simpler operation, shorter extraction time and lower consumption of solvent.

Example 7 Purification by HSCCC

A first solvent system adopted by HSCCC included ethyl acetate, n-butanol, n-hexane, glacial acetic acid, and water; where ethyl acetate, the n-butanol, the n-hexane, the glacial acetic acid, and the water had a volume ratio of 5:2:2:1.5:6; an organic phase and an aqueous phase were mixed in a separatory funnel, and thoroughly equilibrated at room temperature for 15 min to 30 min; upper and lower layers obtained were placed in two conical flasks respectively, the upper phase was as a stationary phase and the lower phase was as a mobile phase. 5 mL of the upper phase and the lower phase were taken, separately, 287 mg of a *Lindera aggregata* leaf extract was dissolved in the two phases of solvents, and the HSCCC was conducted at 800 rpm, 25° C., and an ultraviolet detection wavelength of 280 nm and by using the upper phase as a stationary phase with a retention value of about 40%, and the lower phase as a mobile phase with a flow rate of 2 mL/min; after injection, eluates at 105 min to 115 min, 120 min to 130 min, 170 min to 185 min, and 270 min to 290 min were collected, separately, to obtain quercetin-3-O-β-D-arabinofuranoside, a mixture of quercetin -3-O-β-D-glucoside and quercetin-5-O-β-D-glucoside, quercetin-3-O-rhamnopyranoside, and kaempferol-7-O-α-L-rhamnopyranoside; where there was 10 mg of the mixture of quercetin -3-O-β-D-glucoside and quercetin-5-O-β-D-glucoside using the above solvent system.

Figure 3:
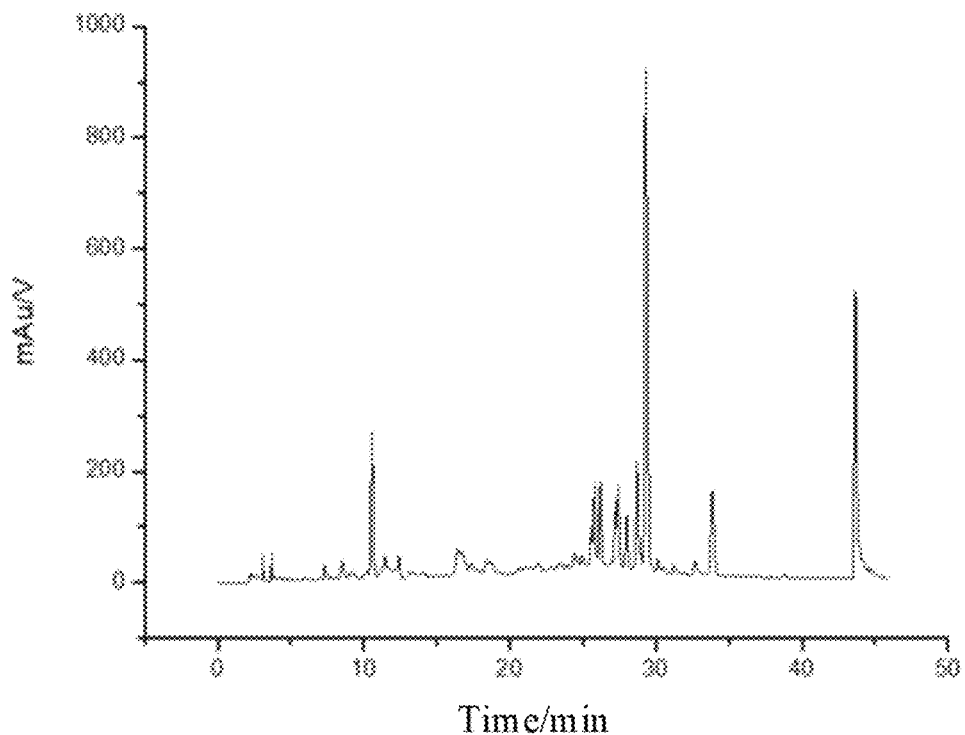
FIG. 3 shows an HPLC chromatogram of a *Lindera aggregata* leaf extract in Example 6 of the present disclosure.
Figure 4:
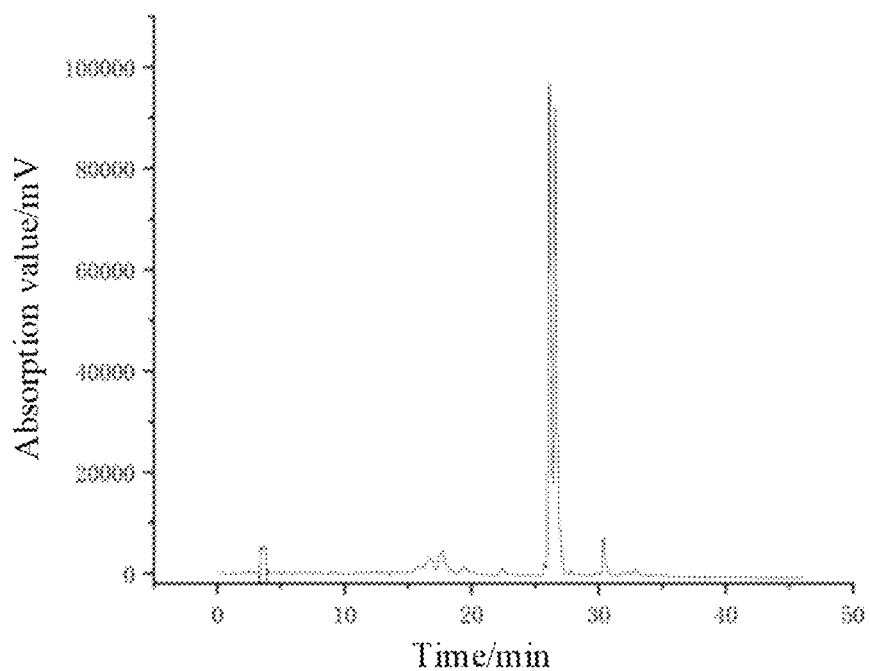
FIG. 4 shows a liquid chromatogram of a mixture of quercetin-3-O-β-D-glucoside and quercetin-5-O-β-D-glucoside in Example 6 of the present disclosure.

FIG. 3 shows an HPLC chromatogram of the *Lindera aggregata* leaf extract; and FIG. 4 shows a chromatogram of the mixture of quercetin-3-O-β-D-glucoside and quercetin-5-O-β-D-glucoside.

Figure 5A:
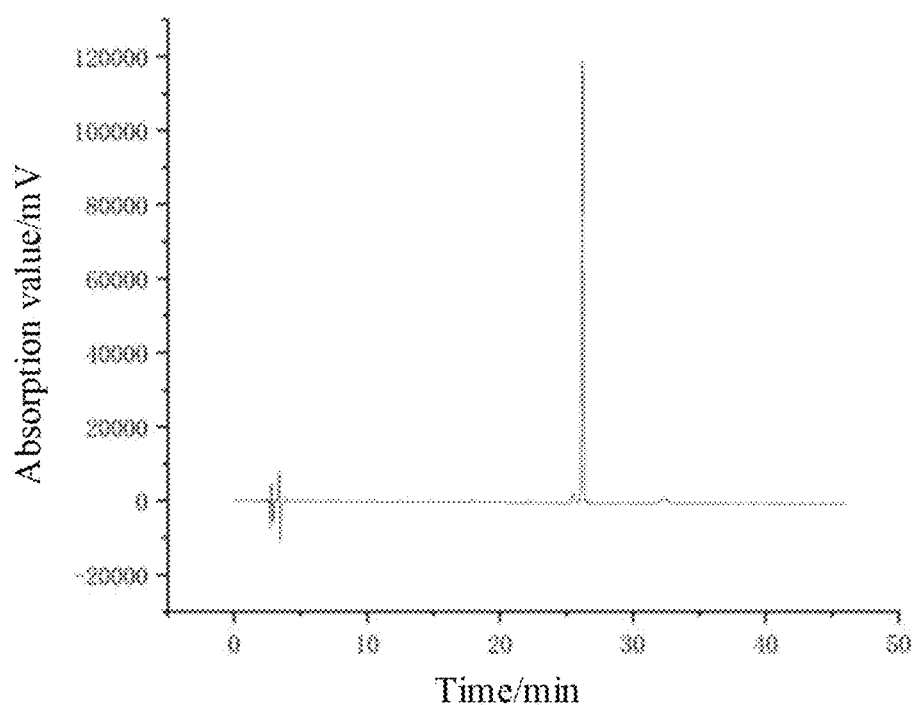
FIG. 5a to FIG. 5b show liquid chromatograms of the quercetin-3-O-β-D-glucoside and the quercetin-5-O-β-D-glucoside in Example 6 of the present disclosure.
Figure 5B:
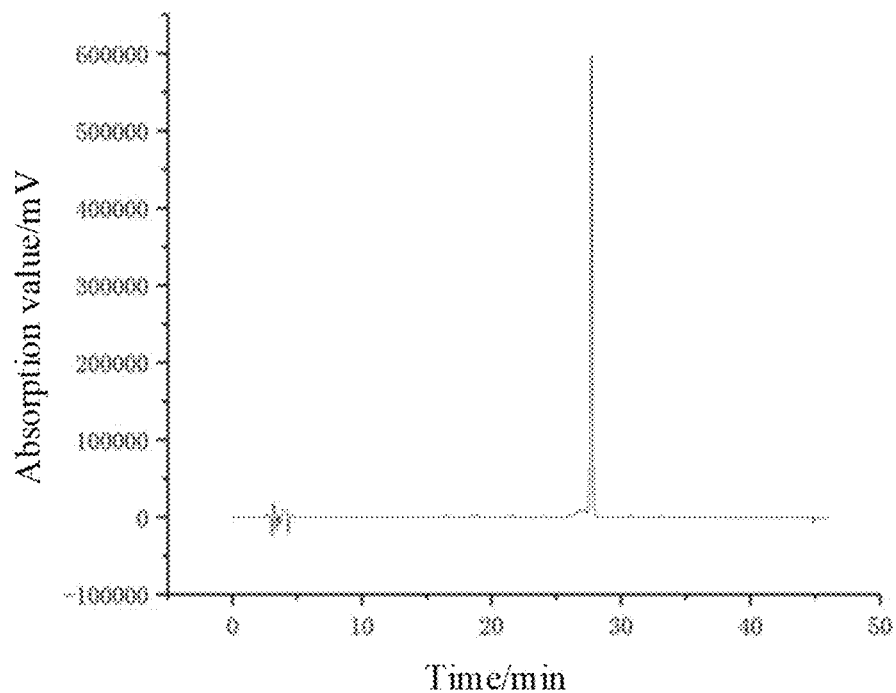

In the present disclosure, the quercetin-3-O-β-D-glucoside and the quercetin-5-O-β-D-glucoside were separated using a second solvent system including the ethyl acetate, the n-butanol and a 0.05 mol/L cyclodextrin aqueous solution at a volume ratio of 9:1:10, where the HSCCC was conducted at 800 rpm, 5° C., and an ultraviolet detection wavelength of 254 nm and by using an upper phase as a stationary phase with a retention value of to 47%, and a lower phase as a mobile phase with a flow rate of 2 mL/min; after injection, the eluates were collected at 670 min to 710 min and 740 min to 790 min, separately. FIG. 5a to FIG. 5b show LC chromatograms of quercetin-3-O-β-D-glucoside and quercetin-5-O-β-D-glucoside, respectively. The results show that a recovery rate of the obtained flavonoids can reach not less than 80%, which is much higher than that of traditional separation and purification.

Figure 6A:
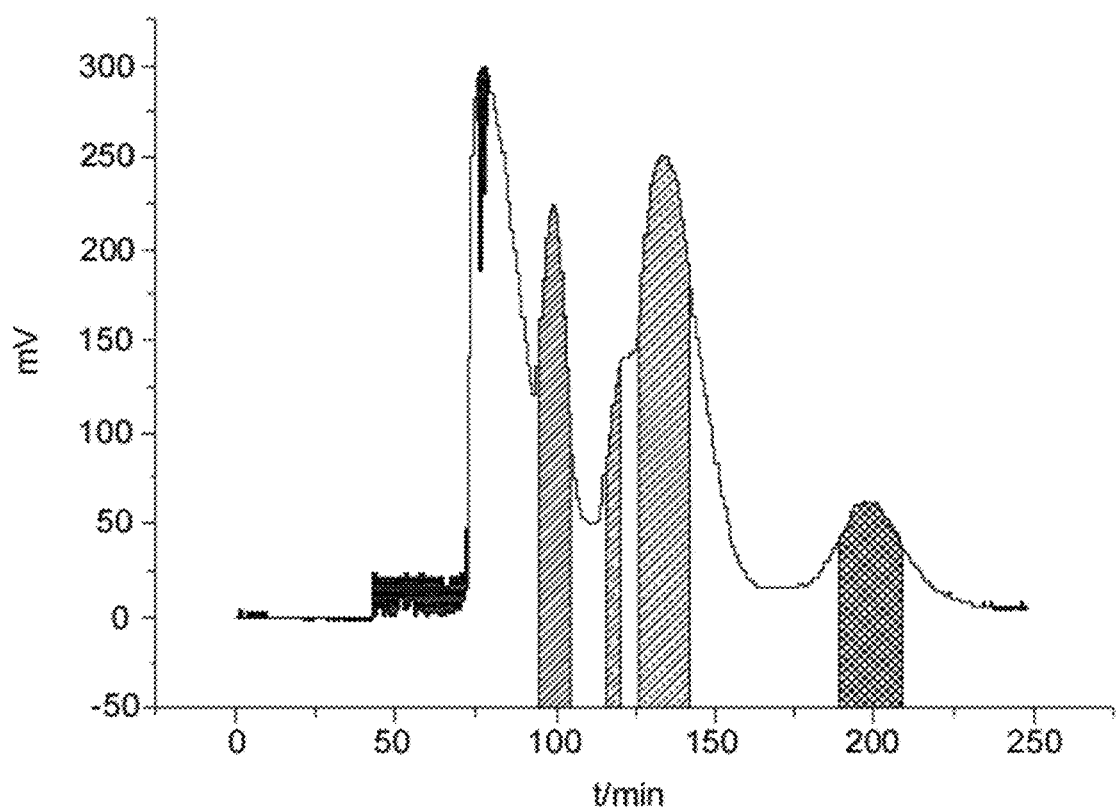
FIG. 6a to FIG. 6b show HSCCC chromatograms of a first solvent system and a second solvent system in Example 6 of the present disclosure.
Figure 6B:
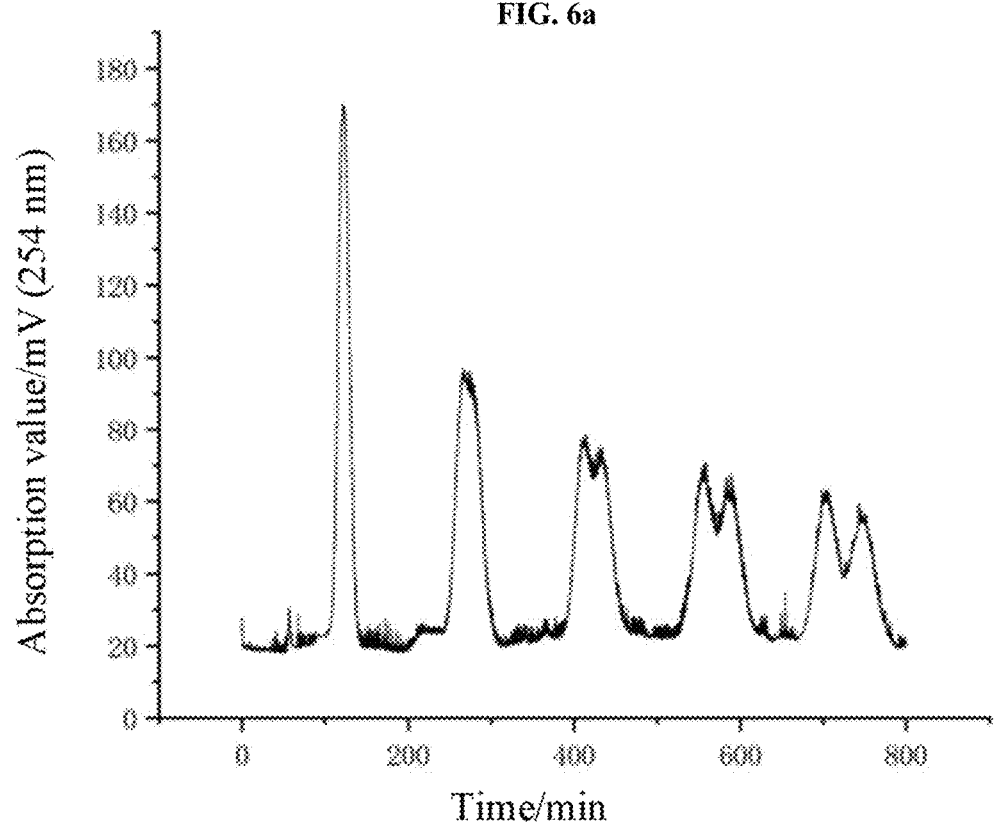

FIG. 6a to FIG. 6b show chromatogram of the first solvent system and the second solvent system, respectively.

In addition, the inventor of this application has also conducted experiments with other raw materials, process operations and process conditions mentioned in this specification with reference to the foregoing examples, and obtained relatively ideal results.

It should be understood that the technical solutions of the present disclosure are not limited to the above-mentioned specific implementation cases. Any technical deformations made according to the technical solutions of the present disclosure without departing from the protection scope of the purpose and claims of the present disclosure falls within the protection scope of the present disclosure.

What is claimed is:

1. A method for extracting and separating flavonoids from *Lindera aggregata* leaves, comprising the following steps:

mixing *Lindera aggregata* leaves with an adsorbent uniformly, conducting extraction by a matrix solid-phase dispersion (MSPD) extraction method, and conducting elution and concentration to obtain a Lindera aggregata leaf extract;

conducting primary separation on the *Lindera aggregata* leaf extract by high-speed counter-current liquid chromatography (HSCCC), to obtain quercetin-3-O-β-D-arabinofuranoside, a mixture of quercetin-3-O-β-D-glucoside and quercetin-5-O-β-D-glucoside, quercetin-3-O-rhamnopyranoside, and kaempferol-7-O-α-L-rhamnopyranoside; wherein a first solvent system used in the primary separation comprises ethyl acetate, n-butanol, n-hexane, glacial acetic acid, and water; and conducting secondary separation on the mixture of quercetin-3-O-β-D-glucoside and quercetin-5-O-β-D-glucoside by the HSCCC, to separate the quercetin-3-O-β-D-glucoside from the quercetin-5-O-β-D-glucoside; wherein a second solvent system used in the secondary separation comprises ethyl acetate, n-butanol, an additive and water, and the additive comprises cyclodextrin.

2. The method according to claim 1, specifically comprising: conducting the primary separation on the *Lindera aggregata* leaf extract by the HSCCC, collecting eluates at 105 min to 115 min, 120 min to 130 min, 170 min to 185 min, and 270 min to 290 min, separately, to obtain the quercetin-3-O-β-D-arabinofuranoside, the mixture of quercetin-3-O-β-D-glucoside and quercetin-5-O-β-D-glucoside, the quercetin-3-O-rhamnopyranoside, and the kaempferol-7-O-α-L-rhamnopyranoside; wherein the HSCCC is conducted at 800 rpm, 25° C., and an ultraviolet detection wavelength of 280 nm and by using an upper phase as a stationary phase, and a lower phase as a mobile phase with a flow rate of 2 mL/min.

3. The method according to claim 1, wherein in the first solvent system, the ethyl acetate, the n-butanol, the n-hexane, the glacial acetic acid and water have a volume ratio of 5:2:2:1.5:6.

4. The method according to claim 1, specifically comprising: conducting the secondary separation on the mixture of quercetin-3-O-β-D-glucoside and quercetin-5-O-β-D-glucoside by the HSCCC, collecting eluates at 670 min to 710 min and 740 min to 790 min, separately, to separate the quercetin-3-O-β-D-glucoside from the quercetin-5-O-β-D-glucoside; wherein the HSCCC is conducted at 800 rpm, 5° C., and an ultraviolet detection wavelength of 254 nm and by using an upper phase as a stationary phase, and a lower phase as a mobile phase with a flow rate of 2 mL/min.

5. The method according to claim 1, wherein
   the cyclodextrin comprises hydroxypropyl-β-cyclodextrin,
   and the hydroxypropyl-β-cyclodextrin and water form an acidic aqueous solution of the hydroxypropyl-β-cyclodextrin with a concentration of 0.05 mol/L.

6. The method according to claim 1, wherein the *Lindera aggregata* leaves and the adsorbent have a mass ratio of 1:0 to 2:1; and/or
   the adsorbent comprises any one of silica gel, alumina, and a molecular sieve SBA-15.

7. The method according to claim 1, specifically comprising the following steps:
   drying, pulverizing, sieving the *Lindera aggregata* leaves, and mixing with the adsorbent for grinding, to form a *Lindera aggregata* leaf mixture;
   conducting elution on the *Lindera aggregata* leaf mixture in a chromatographic column to obtain a Lindera aggregata leaf eluate; and
   concentrating and drying the *Lindera aggregata* leaf eluate to obtain the *Lindera aggregata* leaf extract.

8. The method according to claim 7, wherein the grinding is conducted for 0 min to 6 min.

9. The method according to claim 7, wherein an eluent used in the elution comprises ethanol and/or methanol; and the eluent has a flow rate of 0.5 mL/min to 3 mL/min.

* * * * *